United States Patent [19]
Rooks et al.

[11] Patent Number: 5,892,132
[45] Date of Patent: Apr. 6, 1999

[54] TRANSPORT HYDROXYLATION REACTOR

[75] Inventors: Charles W. Rooks, Houston, Tex.; Anthony K. Uriarte, Pensacola; Michael J. Gross, Cantonment, both of Fla.

[73] Assignee: Solutia Inc., St. Louis, Mo.

[21] Appl. No.: 695,239

[22] Filed: Aug. 8, 1996

[51] Int. Cl.$^6$ ................................................. C07C 37/60
[52] U.S. Cl. ................................................. 568/771; 568/800
[58] Field of Search ................................. 568/771, 800

[56] References Cited

U.S. PATENT DOCUMENTS

| | | | |
|---|---|---|---|
| 4,258,222 | 3/1981 | Möhring et al. | 568/863 |
| 4,982,013 | 1/1991 | Gubelmann et al. | 568/771 |
| 5,001,280 | 3/1991 | Gubelmann et al. | 568/716 |
| 5,019,657 | 5/1991 | Gubelmann et al. | 568/774 |
| 5,055,623 | 10/1991 | Gubelmann et al. | 568/800 |
| 5,110,995 | 5/1992 | Kharitonov et al. | 568/800 |
| 5,171,553 | 12/1992 | Li et al. | 423/239 |
| 5,502,259 | 3/1996 | Zakoshansky et al. | 568/754 |

FOREIGN PATENT DOCUMENTS

| | | |
|---|---|---|
| 0 406 050 A2 | 6/1990 | European Pat. Off. . |
| Hei 5-16179 | 2/1993 | Japan . |
| 2 010 790 | 4/1994 | Russian Federation . |
| 2 116 974 | 3/1993 | United Kingdom . |
| WO 95/27560 | 10/1995 | WIPO . |
| WO 95/27691 | 10/1995 | WIPO . |

OTHER PUBLICATIONS

Dvorak et al. (1970) *Determination Of The Specific Copper Surface Area By Chromatographic Technique*; Journal of Catalysis 18, 108–114, Academic Press, Inc.

Evans et al. (1983) *On The Determination Of Copper Surface Area By Reaction With Nitrous Oxide*; Applied Catalysis 7, 75–83, Elsevier Science Publishers B.V.

Iwamoto et al. (1983) *Catalytic Oxidation By Oxide Radical Ions. 1. One-Step Hydroxylation Of Benzene To Phenol Over Group 5 And 6 Oxides Supported On Silica Gel*; The Journal of Physical Chemistry 87, No. 6, The American Chemical Society.

Ono et al. (1988) *Functionalization Of Benzene By Its Reaction With Nitrogen Oxides Over Solid-Acid Catalysts*, Heterogeneous Catalysis and Fine Chemicals pp. 75–82, Elsevier Science Publishers B.V., Amsterdam.

Suzuki et al. (1988) *Hydroxylation Of Benzene With Dinitrogen Monoxide Over H–ZSM–5 Zeolite*, Chemistry Letters pp. 953–956, The Chemical Society of Japan.

Panov et al. (1990) *The Role Of Iron In $N_2O$ Decomposition On ZSM–5 Zeolite And Reactivity Of The Surface Oxygen Formed*, Journal of Molecular Catalysis 61, 85–97, Elsevier Sequoia.

Sobolev et al. (1991) *Anomalously Low Bond Energy Of Surface Oxygen On FeZSM–5 Zeolite*, Mendeleev Communications, No. 1, pp. 29–30.

Zholobenko (1993) *Preparation Of Phenol Over Dehydroxylated HZSM–5 Zeolites*, Mendeleev Communications, pp. 23–24.

Hafele et al. (1996) *Hydroxylation of Benzene on ZSM5 Type Catalysts*, DGMK–Conference, Catalysis On Solid Acids And Bases pp. 243–251.

Vereshchagin et al, *Conversion Of Ethane On Zeolite Catalysts In The Presence Of Oxygen And Nitrogen(I) Ox De, Izv. Akad. Nauk SSSR*, (1988), 1718–1722 The enclosed is an English abstract translated from a Russian article.

Li et al. (1992) *Catalytic Decomposition Of Nitrous Oxide On Metal Exchanged Zeolites*; Applied Catalysis B: Environmental 1, L21–29; Elsevier Science Publishers B.V., Amsterdam.

Sobolev et al. (1993) *Catalytic Properties Of ZSM–5 Zeolites In $N_2O$ Decomposition: The Role Of Iron*; Journal of Catalysis 139, 435–443; Academic Press, Inc.

Sobolev et al. (1993) *Stoichiometric Reaction Of Benzene With α–Form Of Oxygen On Fezsm–5 Zeolites. Mechanism Of Aromatics Hydroxylation By $N_2O$*; Journal of Molecular Catalysis 84, 117–124; Elsevier Science Publishers B.V., Amsterdam.

Panov et al. (1992) *Oxidation Of Benzene To Phenol By Nitrous Oxide Over Fe–ZSM–5 Zeolites*; Applied Catalysis A: General 82, 31–36, Elsevier Science Publishers B.V., Amsterdam.

Kharitonov et al. (1993) *Ferrisilcate Analogs Of ZSM–5 Zeolite As Catalysts For One Step Oxidation Of Benzene To Phenol*; Applied Catalysis A: General 98, 33–43, Elsevier Science Publshers B.V., Amsterdam.

(List continued on next page.)

*Primary Examiner*—Robert Gerstl
*Attorney, Agent, or Firm*—Arnold White & Durkee

[57] ABSTRACT

A continuous process for converting benzene or a derivative thereof to phenol or a derivative thereof comprises continuously activating α-sites on a zeolite catalyst by contacting the catalyst with a free oxidant activator, thereby producing an activated zeolite hydroxylation catalyst, and separately and continuously contacting benzene or a derivative thereof with the activated zeolite catalyst, thereby producing phenol or a derivative thereof. The benzene or derivative thereof can be separately contacted with the activated zeolite catalyst by (a) contacting in a reaction vessel that is physically separate and distinct from the vessel in which the catalyst is contacted with the free oxidant activator, (b) contacting in a zone of a vessel that is separate from the zone in that same vessel in which the catalyst is contacted with the free oxidant activator, or (c) contacting with the catalyst in a reaction vessel in a first time pulse, with the benzene or derivative thereof being contacted with the activated zeolite catalyst in a second time pulse in the same reaction vessel which does not overlap substantially with the first time pulse.

11 Claims, 1 Drawing Sheet

OTHER PUBLICATIONS

Burch et al. (1993) *Factors Affecting The Deactivation Of Various Zeolites Used As Catalysts For The Direct Partial Oxidation Of Benzene To Phenol*; Applied Catalysis A: General 106, 167–183, Elsevier Science Publishers B.V., Amsterdam.

Burch et al. (1993) *Investigation Of Zeolite Catalysts For The Direct Parial Oxidation Of Benzene To Phenol*; Applied Catalysis A: General 103, 135–162, Elsevier Science Publishers B.V., Amsterdam.

Burch et al. (1993) *Direct Partial Oxidation Of Benzene To Phenol on Zeolite Catalysts*; Applied Catlysis A: General 86, 139–146, Elsevier Science Publishers B.V., Amsterdam.

Panov et al. (1993) *Oxidative Hydroxylation Using Dinitrogen Monoxide; A Possible Route For Organic Synthesis Over Zeolites*, Applied Catalysis A: General, 98, 1–20, Elsevier Science Publishers B.V., Amsterdam.

Derwent abstract; JP 5 009 142.

Derwent abstract, JP 4 334 333.

Derwent abstract, JP 4 021 645.

Derwent abstract, JP 6 009 464.

Derwent abstract, JP 6 040 976.

Derwent abstract, EP 406 050.

TRANSPORT HYDROXYLATION REACTOR

BACKGROUND OF THE INVENTION

The present invention relates to an improved process and reactor system for the hydroxylation of benzene or derivatives thereof to form phenol or related compounds.

Phenol or a derivative thereof can be produced by a single-step oxidative hydroxylation of benzene or a derivative thereof, using nitrous oxide over a catalyst. For example, PCT publication WO 95/27560 describes such a process in which benzene is combined with nitrous oxide over a zeolite catalyst that has been hydrothermally treated, converting the benzene to phenol. It is believed that specific active sites on the zeolite, referred to as $\alpha$-sites, are responsible for the desirable conversion in such a process. After a batch of catalyst is used for a time in the process, some of the $\alpha$-sites become deactivated, and the catalyst must then be reactivated.

In prior art processes of the general type described above, reactivation of the zeolite catalyst has been done in situ with an oxidant activator such as nitrous oxide. However, this presents several problems. For example, the intermediates and products of the hydroxylation reaction are generally more reactive than the reactant. This often leads to production of undesirable over-oxidated byproducts instead of maximum production of the desired end product. Moreover, the free oxidant used to activate the $\alpha$-sites is generally less selective than the $\alpha$-sites, which also contributes to increased production of undesirable byproducts. Another problem is that explosive mixtures can sometimes be formed between the reactant and the free oxidant activator, which can present a safety problem.

These problems constrain the practical operation of a commercial process. In general, in situ reactivation of the catalyst leads to a compromise choice of process conditions because the preferred conditions for activating the $\alpha$-sites may not be the optimum conditions for the hydroxylation reaction. In particular, with in situ activation of $\alpha$-sites, reaction conditions must be sought that minimize raw material, energy, and capital consumption while forming a safe and commercially viable operation. Inevitably this involves a compromise among these three major cost factors. For example, to maintain operation outside of flammability regions, inert diluents are often added that must eventually be separated and recycled, requiring additional capital and energy. Also, because of the nonselective nature of the oxidant activator, the reactions are run at relatively low reactant conversion to minimize over-oxidation to undesired byproducts. This results in a compromise between raw material cost and energy usage for recycle.

A need exists for processes and catalysts having improved performance, so that the conversion of an aromatic hydrocarbon such as benzene to phenol or another desired product can be made more economical. One potential way of improving catalyst performance is by selective introduction of sites for hydroxylation, for example by introducing iron into the catalyst. However, introduction of active iron via synthesis can present complications.

SUMMARY OF THE INVENTION

In the present invention, instead of in situ activation of a benzene hydroxylation catalyst, the catalyst is activated (loaded) via nitrous oxide or another suitable oxidant in one vessel, zone, or time pulse. The activated catalyst, having loaded $\alpha$-sites, is then contacted with the reactant (e.g., benzene) stream in a separate vessel, zone, or time pulse. After the catalytic reaction has proceeded for a time, the catalyst is returned to the first vessel or zone where depleted $\alpha$-sites on the catalyst are then reactivated, or the catalyst is similarly activated in a sequential time pulse. In this manner, the free oxidant activator does not come into substantial contact with the reactants, intermediates, or products.

One aspect of the present invention concerns a process for catalytic hydroxylation of an aromatic compound. One embodiment is a continuous process for converting benzene or a derivative thereof to phenol or a derivative thereof that includes the steps of continuously activating $\alpha$-sites on a zeolite catalyst by contacting the catalyst with a free oxidant activator, thereby producing an activated zeolite hydroxylation catalyst, and separately and continuously contacting benzene or a derivative thereof with the activated zeolite catalyst, thereby producing phenol or a derivative thereof.

"Separately" in this context can have any one of the following meanings. The benzene or derivative thereof can be separately contacted with the activated zeolite catalyst by contacting in a reaction vessel that is physically separate and distinct from the vessel in which the catalyst is contacted with the free oxidant activator. Alternatively, it can be separately contacted with the activated zeolite catalyst by contacting in a zone of a vessel that is separate from the zone in that same vessel in which the catalyst is contacted with the free oxidant activator. As another alternative, the free oxidant activator can be contacted with the catalyst in a first time pulse and the benzene or a derivative thereof contacted with the activated zeolite catalyst in a second time pulse which does not overlap substantially with the first time pulse.

One specific embodiment of the invention is a continuous process that comprises the steps of (a) continuously feeding a free oxidant activator to a catalyst activation pressure vessel and contacting the free oxidant activator with a zeolite hydroxylation catalyst in that vessel at a temperature between approximately 200–500° C., thereby producing an activated zeolite hydroxylation catalyst, (b) carrying activated zeolite hydroxylation catalyst through a conduit from the catalyst activation pressure vessel to an hydroxylation reactor pressure vessel which is separate from the catalyst activation pressure vessel, (c) continuously feeding benzene or a derivative thereof to the hydroxylation reactor pressure vessel, in which the benzene or derivative thereof is contacted with the activated zeolite catalyst at a temperature between approximately 100–500° C., thereby producing phenol or a derivative thereof, and thereby partially deactivating the zeolite hydroxylation catalyst, and (d) carrying partially deactivated zeolite hydroxylation catalyst through a conduit from the hydroxylation reactor pressure vessel to the catalyst activation pressure vessel.

Another aspect of the present invention concerns an hydroxylation reactor system that comprises a catalyst activation reactor, in which a zeolite catalyst is contacted with a free oxidant activator, a hydroxylation reactor in which an aromatic compound such as benzene or a derivative thereof is contacted with a zeolite catalyst, and at least two conduits between the catalyst activation reactor and the hydroxylation reactor, one of the conduits being adapted for carrying activated catalyst from the catalyst activation reactor to the hydroxylation reactor, and the other conduit being adapted for carrying catalyst that is at least partially deactivated from the hydroxylation reactor to the catalyst activation reactor.

In this aspect of the invention, the catalyst activation reactor and the hydroxylation reactor can be separate pressure vessels with the conduits being pipes connected to each of the two separate pressure vessels. Alternatively, the catalyst activation reactor and the hydroxylation reactor can be different zones in a single pressure vessel, with the conduits being passages from one zone to another in this single pressure vessel.

A particular embodiment of this aspect of the invention comprises a catalyst activation reactor pressure vessel, in which a zeolite catalyst is contacted with a free oxidant activator, a hydroxylation reactor pressure vessel which is separate from the catalyst activation pressure vessel and in which benzene or a derivative thereof is contacted with a zeolite catalyst, an activated catalyst supply conduit connecting the two pressure vessels for carrying activated catalyst to the hydroxylation reactor pressure vessel, and a deactivated catalyst return conduit connecting the two pressure vessels for carrying catalyst that is at least partially deactivated from the hydroxylation reactor pressure vessel to the catalyst activation reactor pressure vessel.

The present invention separates the activation of the $\alpha$-sites on the zeolite catalyst from the reaction of those sites with the aromatic hydrocarbon, substantially reducing the problem of excessive production of undesirable byproducts such as over-oxidated compounds. The present invention also permits the selection of optimal process conditions for the activation and reaction steps or phases, instead of having to settle for a compromise between the two as was necessary in prior art processes. This freedom to optimize conditions for the two steps can permit a greater conversion of reactant to desired product. Further, since the free oxidant activator is kept substantially separate from the reactant, explosive mixtures of the two are much less likely to be formed.

DESCRIPTION OF ILLUSTRATIVE EMBODIMENTS

Figure 1:
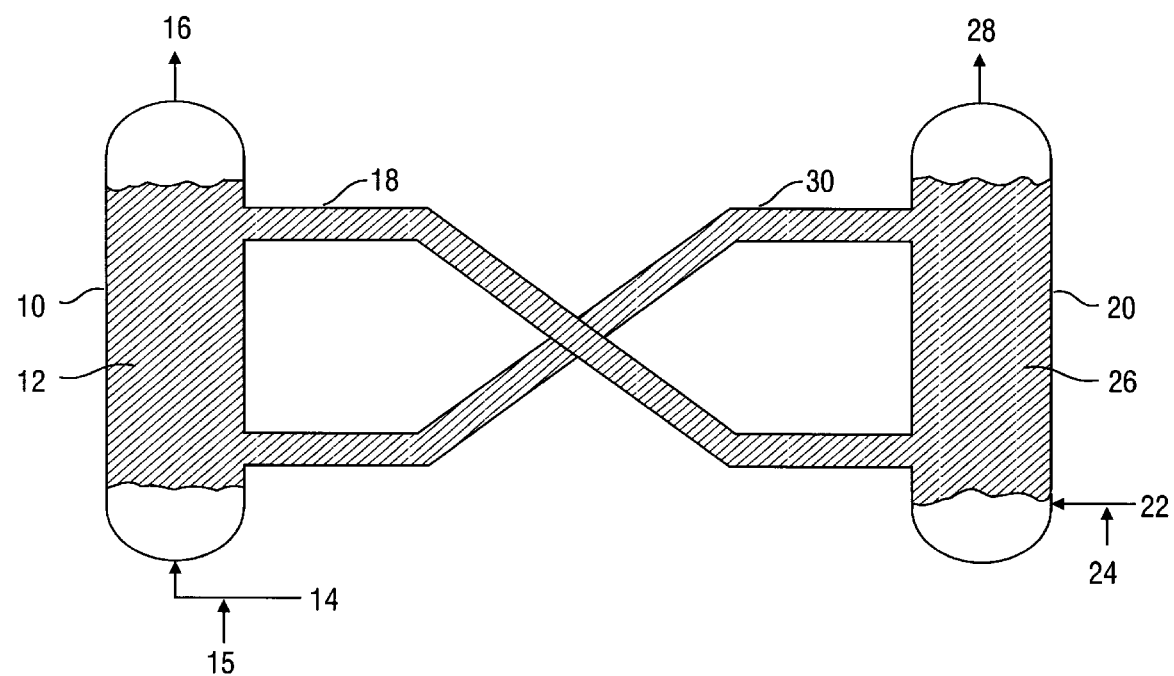
FIG. 1 shows in schematic form an hydroxylation process and reactor system in accordance with the present invention.

One embodiment of the present invention is shown in schematic form in FIG. 1. In this embodiment, catalyst activation and hydroxylation of benzene take place in two separate pressure vessels, which are connected by two conduits for transfer of the catalyst between the two vessels.

A catalyst activation pressure vessel 10 contains particles of a zeolite hydroxylation catalyst 12. A feed stream 14 provides a continuous flow of a free oxidant activator, such as nitrous oxide, to the catalyst activation vessel 10. Optionally an inert diluent 15 such as $N_2$ can be included in the feed stream 14. In the catalyst activation vessel 10 the catalyst 12 contacts the free oxidant activator, resulting in the activating (loading) of $\alpha$-sites in the catalyst. A gas stream 16, primarily composed of nitrogen, exits the vessel 10.

The activated catalyst particles are then carried through a first conduit 18 to a reaction pressure vessel 20. A pump (not shown) can be used to assist in moving the activated catalyst to the reaction vessel 20. In that vessel 20, the $\alpha$-oxygen loaded catalyst is used to convert an aromatic hydrocarbon, e.g. benzene, into its hydroxylated derivative, e.g. phenol. A reactant feed stream 22 supplies the benzene to the vessel 20, and optionally an inert diluent 24 such as nitrogen can be supplied in the feed stream also. In the presence of the activated catalyst particles 26, the benzene is converted to phenol, which is removed in a product stream 28.

The catalyst will tend to become deactivated after the reaction proceeds for a time, so at least a portion of the catalyst particles 26 are then carried back to the catalyst activation vessel 10 through a second conduit 30. A pump (not shown) can be used to assist this transfer through the conduit 30. In this manner, the process can operate continuously, constantly reactivating catalyst while keeping that step in the process physically separate from the ongoing hydroxylation reaction.

The temperature in the catalyst activation vessel 10 at which the catalyst particles are contacted with the free oxidant activator is preferably between approximately 200–500° C. The temperature in the reaction vessel 20 at which the benzene or derivative thereof is contacted with the activated zeolite catalyst is preferably between approximately 100–500° C. Persons skilled in the art will be able to select particular temperatures and other process conditions based on the desired product, design kinetics, and other circumstances. For example, in the conversion of benzene to phenol, suitable temperatures for the catalyst activation and the reaction would be 350° C. and 450° C., respectively.

The residence time can preferably range from approximately 1–5 sec. in the catalyst activation vessel and between approximately 1–5 sec. in the hydroxylation reaction vessel.

There will typically be some buildup of coke on the catalyst as time passes. This can be removed at a number of points in the process. One suitable approach is to remove a slipstream of catalyst passing through the second conduit 30, remove the coke from that catalyst by means well known to those skilled in the art, and then return the catalyst to the stream flowing through the second conduit 30 to the catalyst activation vessel 10.

Aromatic compounds can be hydroxylated using the process of the present invention. Preferred aromatic compounds for use as reactants have from about 6–18 carbon atoms, and can optionally be substituted with one or more substituents such as halogens, aliphatic hydrocarbons having from 1–6 carbon atoms, hydroxyl, carboxy, amino, nitro, or thio groups. The present invention is especially useful in the hydroxylation of benzene and benzene derivatives such as chlorobenzene, fluorobenzene, toluene, ethylbenzene, and the like, into the corresponding substituted phenol. If phenol itself is the benzene derivative used as the reactant, the reaction products can include polyols such as hydroquinone, resorcinol, and catechol.

Preferred zeolite catalysts for use in the present invention include ZSM-5 and ZSM-11. Such zeolites are available from vendors such as Zeolyst International, UOP, Mobil, and others. The catalyst preferably has an iron content of approximately 0.1–0.3 weight %.

Nitrous oxide is the preferred free oxidant activator used to replenish the hydroxylation catalyst with oxygen.

The optional diluent added to the feed can be, for example, nitrogen, argon, or carbon dioxide. Persons skilled in the art would be able to select other suitable diluents that would be substantially inert in the process.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A process for hydroxylating an aromatic compound, comprising the steps of:

activating $\alpha$-sites on a zeolite catalyst by contacting catalyst with nitrous oxide, thereby producing an activated zeolite hydroxylation catalyst; and separately contacting an aromatic compound with the activated zeolite catalyst, thereby producing a hydroxylated derivative of the aromatic compound.

2. The process of claim 1, where the aromatic compound is contacted with the activated zeolite catalyst in a reaction vessel that is separate from the vessel in which the catalyst is contacted with the nitrous oxide.

3. The process of claim 1, where the aromatic compound is contacted with the activated zeolite catalyst in a zone of a vessel and the catalyst is contacted with the nitrous oxide in a separate zone in that same vessel.

4. The process of claim 1, where the zeolite catalyst is contacted with the nitrous oxide in a first time pulse and the aromatic compound is contacted with the activated zeolite catalyst in a second time pulse which does not substantially overlap with the first time pulse.

5. The process of claim 1, where the activation of $\alpha$-sites on the catalyst by contacting the catalyst with nitrous oxide is done continuously and the aromatic compound is contacted with the activated catalyst continuously.

6. The process of claim 1, where the aromatic compound is benzene and the hydroxylated derivative is phenol.

7. The process of claim 1, where the catalyst is contacted with the nitrous oxide at a temperature between approximately 200–500° C.

8. The process of claim 1, where the aromatic compound is contacted with the activated zeolite catalyst at a temperature between approximately 100–500 ° C.

9. The process of claim 1, further comprising feeding an inert diluent with the nitrous oxide.

10. A continuous process for converting benzene or a derivative thereof to phenol or a derivative thereof, comprising the steps of:

continuously feeding nitrous oxide to a catalyst activation pressure vessel and contacting the nitrous oxide with a zeolite hydroxylation catalyst in that vessel at a temperature between approximately 200–500° C., thereby producing an activated zeolite hydroxylation catalyst;

carrying activated zeolite hydroxylation catalyst through a conduit from the catalyst activation pressure vessel to an hydroxylation reactor pressure vessel which is separate from the catalyst activation pressure vessel;

continuously feeding benzene or a derivative thereof to the hydroxylation reactor pressure vessel, in which the benzene or derivative thereof is contacted with the activated zeolite catalyst at a temperature between approximately 100–500° C., thereby producing phenol or a derivative thereof; and carrying partially deactivated zeolite hydroxylation catalyst through a conduit from the hydroxylation reactor pressure vessel to the catalyst activation pressure vessel.

11. The process of claim 10, further comprising continuously feeding an inert diluent to the catalyst activation reactor pressure vessel.

* * * * *